US006932598B1

(12) United States Patent
Anderson

(10) Patent No.: US 6,932,598 B1
(45) Date of Patent: Aug. 23, 2005

(54) DEVICE AND METHOD OF MOLAR DISTALIZATION AND MANDIBULAR PROTRACTION

(76) Inventor: Ross W. Anderson, 8510 N. Canton Center Rd., Canton, MI (US) 48178

( * ) Notice: Subject to any disclaimer, the term of this patent is extended or adjusted under 35 U.S.C. 154(b) by 206 days.

(21) Appl. No.: 10/243,038

(22) Filed: Sep. 13, 2002

Related U.S. Application Data

(60) Provisional application No. 60/347,686, filed on Jan. 11, 2002.

(51) Int. Cl.$^7$ ............................................... A61C 3/00
(52) U.S. Cl. ............................. 433/19; 433/18; 433/23
(58) Field of Search ............................. 433/18, 19, 20, 433/21, 22, 23, 24

(56) References Cited

U.S. PATENT DOCUMENTS

| 1,597,529 | A | | 8/1926 | Leonard | 433/19 |
| 3,416,228 | A | | 12/1968 | Grimmett | 433/19 |
| 3,798,773 | A | | 3/1974 | Northcutt | 433/19 |
| 4,382,783 | A | | 5/1983 | Rosenberg | 433/19 |
| 4,708,646 | A | | 11/1987 | Jasper | 433/19 |
| 5,443,384 | A | | 8/1995 | Franseen et al. | 433/18 |
| 5,848,891 | A | | 12/1998 | Eckhart et al. | 433/19 |
| 6,099,304 | A | | 8/2000 | Carter | 433/19 |
| 6,368,106 | B1 | * | 4/2002 | Clark | 433/19 |
| 6,726,473 | B1 | * | 4/2004 | Guray | 433/6 |

OTHER PUBLICATIONS

Edward H. Angle, M.D., (Book), "Treatment of Malocclusion of the Teeth," 7th Ed., 1907, (pp. 499-502 and FIG 258-9), S.S. White Dental Co., Philadelphia.

* cited by examiner

*Primary Examiner*—John J Wilson
(74) *Attorney, Agent, or Firm*—Charles W. Chandler

(57) ABSTRACT

The present invention is a device (18) and method for applying posteriorly directed pressure to a patient's upper posterior tooth, and anteriorly directed pressure to the lower teeth and lower jaw (50). The device includes a tooth attachment (22) fixed to a lower posterior tooth. A mounting base (20) is connected to the tooth attachment, and serves to mount a bumper unit (62), which extends from the lower posterior tooth to the upper posterior tooth. The bumper unit includes a bite bumper (32), for contacting the upper tooth. In the patient's retruded or uncorrected jaw position, the obstruction surface (38) of the bite bumper strikes the occlusal surface (41) of the upper posterior tooth, obstructing full closure of the jaws. Because this obstruction causes discomfort to the patient, the lower jaw is protruded into the forward or corrected jaw position. During protrusion, the bite bumper slides forwardly and upwardly into the adjacent opening (54) immediately anterior to the upper posterior tooth. The functional pressure generated by this jaw posture urges the upper posterior tooth in a posterior direction and the mandibular jaw in a forward direction. Over a period of time, the dental bite and jaw position become stable in the corrected jaw position.

16 Claims, 4 Drawing Sheets

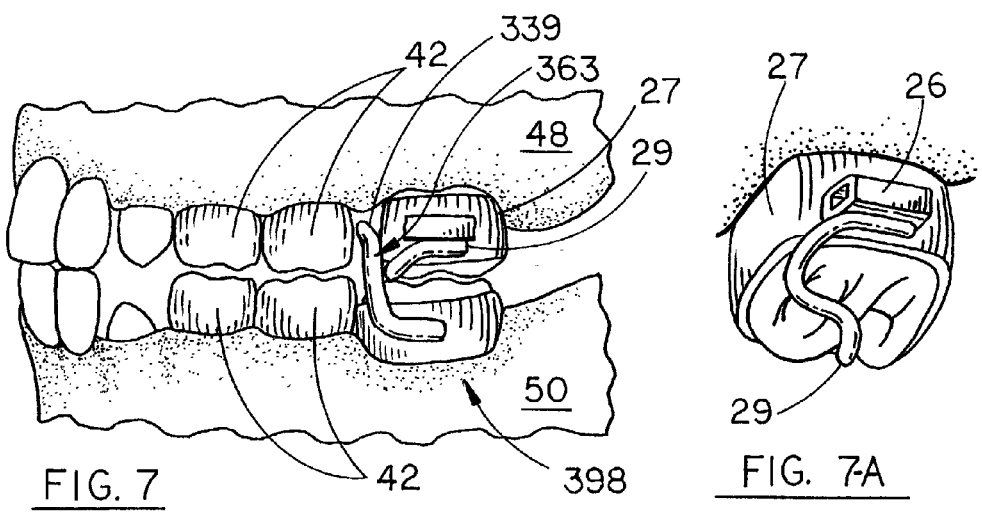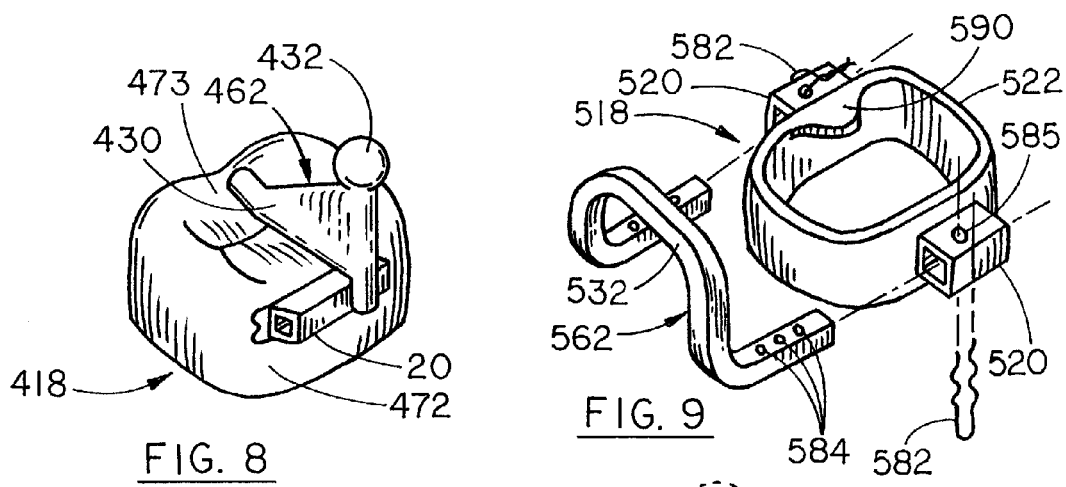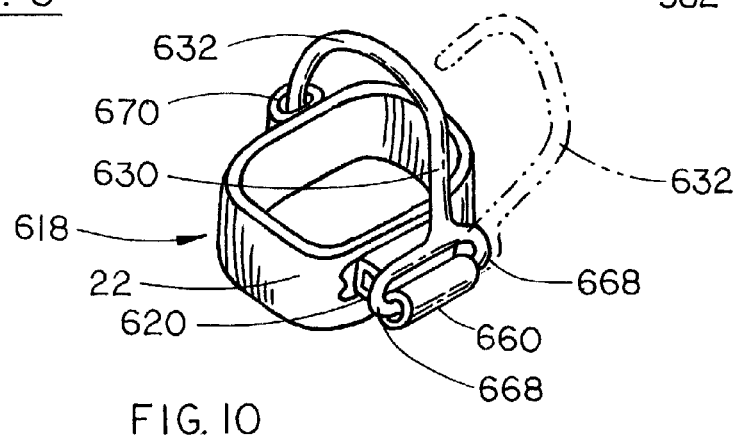

DEVICE AND METHOD OF MOLAR DISTALIZATION AND MANDIBULAR PROTRACTION

CROSS-REFERENCE TO RELATED APPLICATION

This application claims the benefit of Provisional Patent Application Ser. No. 60/347,686 filed Jan. 11, 2002.

BACKGROUND

This invention relates to devices and methods for exerting a posteriorly-directed or distalizing force to a patient's upper posterior tooth, and an anteriorly-directed or protraction force to the lower jaw and teeth. The invention is particularly directed to orthodontic devices and methods which include a tooth attachment fixed to a patient's lower posterior tooth, and also include a bite bumper for transmitting the natural lower jaw pressure to an upper posterior tooth.

Many patients suffer from a bite condition in which the upper anterior teeth exhibit excessive horizontal overbite, termed "overjet", and the lower molars bite too far back relative to the upper molars. This bite imbalance is called a "Class II malocclusion". The imbalance can result from the lower (mandibular) jaw being too short, or the upper (maxillary) jaw being too far forward. Several devices, called "functional appliances", have been used by orthodontists to hold the lower jaw forward from its retruded, uncorrected condition, and after a period of time wearing such a functional appliance, the bite becomes stable in the advanced, corrected position. This correction is due to shifting of the teeth within the jaws, and to differential growth caused by the appliance. To achieve this correction, the upper teeth are shifted posteriorly and the lower teeth and jaw are shifted anteriorly, reducing the overjet.

Overjet can also be treated by fixed intraoral distalizing devices which work exclusively on teeth in the upper jaw, using the roof of the mouth and the anterior teeth as an anchor to push posteriorly on the molar teeth. The upper teeth are moved posteriorly, or "distalized", in two stages. In Stage I the upper molars are distalized with a fixed intraoral device or with standard orthodontic braces. Then in Stage II the remaining upper anterior teeth are distalized, frequently using elastic bands pulling back from the lower teeth and braces. During Stage II, forward relapse of molar correction is common. To minimize this relapse, a Nance button appliance is often attached to the molars as an anchor, holding them posteriorly while the anterior teeth are being retracted. Examples of fixed intraoral distalizing devices include the Jones Jig, the Hilgers pendulum, and the distal jet appliances. Disadvantages of these distalizing devices include bulky material in the palate area, and fast relapse of the molars to their forward position after device removal. The major advantage of fixed distalizing devices is that patient compliance is ensured since the device is fixed to the teeth.

Another group of devices correct the excessive overjet by holding the lower jaw forward and moving the upper teeth rearward, shifting the teeth in both jaws to a corrected position. These devices, commonly referred to as "functional appliances", apply posteriorly-directed pressure to the upper teeth, and anteriorly-directed or protraction pressure to the lower jaw and teeth. Examples of such devices include Herbsts, twin blocks, activators, bionators, Frankels, and class II elastics. An advantage of functional appliances is that the natural pressure of the dental bite and jaws is redirected to move the teeth. Because the patient continuously bites, chews, and clenches throughout the day, constant gentle pressure is applied to the teeth. One major disadvantage of these appliances is that they are usually removable, resulting in poor patient compliance. A second disadvantage is that they are generally bulky, interfering with eating, speech, and comfort. Thirdly, these appliances generally have a fixed connection between the upper and lower jaws, which can limit jaw movement, and is bulky and unsightly.

U.S. Pat. No. 3,416,228 to Grimmett discloses a device fixed to the lower molars, which has a labial wire bow contacting the lower anterior teeth, giving attachment to a second bow which fits around the front surfaces of the upper anterior teeth. Because it cannot be removed by the patient, the '228 device solves the problem of poor patient compliance. It corrects the class II malocclusion by protracting the mandible when the patient bites together, and applies posteriorly-directed pressure to the maxilla. The chief disadvantages of the '228 device include its inability to be used simultaneously with orthodontic braces, and its poor cosmetics.

U.S. Pat. No. 4,382,783 to Rosenberg discloses a device comprising two hinges with telescoping members to join an upper and lower molar on both sides of the mouth, correcting a class II malocclusion by protracting the lower jaw. The '783 device has the disadvantages of permanently connecting the jaws which limits motion, and having parts projecting outward toward the cheeks of the patient, which can cause soft-tissue discomfort.

U.S. Pat. No. 5,848,891 to Eckhart et al discloses a device having a first member attached to the upper molar and a second member attached to the lower molar, both members projecting outward toward the cheek. The members of the '891 device are designed to prevent complete closure of the jaws in the uncorrected or retruded jaw position. Biting in this position can put extreme vertical pressure on the members, transmitting a torsion force to the molar bands, thereby resulting in frequent breakage of the bands. For this reason, a stainless steel veneer crown is frequently used to give attachment to each member. Attached to the upper and lower first molar teeth, the crowns are stronger than orthodontic bands, but are difficult to remove after treatment is completed. Another disadvantage of the '891 device is that it requires fabrication by a dental laboratory, and requires two separate appointments: a first to take a dental impression, and a second for delivery after laboratory fabrication.

U.S. Pat. No. 6,099,304 to D. Carter discloses a device having an adjustment assembly on the upper molar, and a placement assembly on the lower molar, both assemblies projecting outward toward the cheek. The '304 device, as with the '891 device, prevents complete closure of the jaws in the uncorrected bite position, causing protraction of the lower jaw to allow complete closure into the corrected bite position.

Some of these prior-art devices, such as U.S. Pat. Nos. 3,416,228 and 5,443,384 have permanent parts near the surface of the teeth which can trap food and Interfere with good oral hygiene. In addition, the device of U.S. Pat. No. 4,382,783 permanently connects the jaws which can limit jaw movement.

Other devices, such as those of U.S. Pat. Nos. 5,848,891 and 6,099,304 have parts projecting laterally towards the cheek of the patient's mouth, which can cause painful biting of the cheeks. Furthermore, both of these devices employ two members for each side of the mouth, so that each patient generally requires four members. This degree of complication generally requires construction by a dental laboratory, which requires two patient visits for device delivery to the patient. An additional disadvantage of these two devices is that, in the retruded jaw position, the patient's strong vertical biting forces can cause breakage of the tooth band, since the vertical force applied to the member is far away from the tooth, located more laterally near the patient's cheek. This transmits a torsion force to the band causing breakage and loosening. To prevent breakage, these members are usually attached to stainless steel crowns over the molar teeth, which have the distinct disadvantage of being difficult to remove.

Therefore, it would be highly advantageous to have a device and method of treating excessive overjets, which the patient cannot remove, and which take advantage of the natural bite pressure to distalize the upper teeth. It would also be beneficial to have such a device and method which do not permanently connect the jaws, allowing greater comfort and jaw movement, and still providing a non-removable device to ensure patient compliance. Additionally, it would be advantageous for this invention to allow the teeth in both jaws to be moved orthodontically with braces.

It would also be helpful for the device to be simple in design, having only one member for each side of the patient's mouth, allowing it to be prefabricated. This simple design could be prefabricated in a variety of sizes, and would require one patient appointment, rather than two, for delivery of the device to the patient. In addition, it would be beneficial for the point of biting force on the device to be located near the tooth surface, rather than laterally near the cheek, to prevent breakage and allow for the use of an orthodontic band as a means of tooth attachment. Furthermore, it would be desirable for the invention to be less visible, to enhance cosmetic appeal, and to be less bulky than traditional devices, enhancing patient comfort. Finally, it would be helpful for the device and method to avoid parts positioned near the patient's cheek, which can result in painful biting of the cheek and can interfere with proper tooth brushing.

SUMMARY

This invention is directed to a device and method for applying posteriorly-directed or distalizing pressure to an upper posterior tooth and providing an anteriorly-directed force to the patient's lower teeth and jaw. The invention is designed to operate on an upper posterior tooth having a opening directly to its anterior. Prior to installing the device, the opening is created with a fixed intraoral distalizing device, or with an opening mechanism, such as a coil or loop, on standard orthodontic braces. Alternatively, the opening could be created by extracting a tooth.

The device includes a tooth attachment, usually a commercially-available orthodontic band, fixed to a lower posterior tooth. A mounting base is connected to the outer surface of the attachment. The mounting base can be connected to either the lingual (tongue-side) surface, the buccal (cheek-side) surface, or to the occlusal (biting) surface of the tooth attachment. Extending vertically from the mounting base is a holding leg, for holding the bite bumper at the proper vertical height above the mandibular occlusal plane. In some cases, the device may have two holding legs, one connected to the buccal side of the attachment, and one on the lingual side. Fixed to the holding leg is a bite bumper, for applying distal pressure to the anterior or mesial surface of an upper posterior tooth.

The device is mounted on the lower posterior tooth in such a way that, in the uncorrected jaw position, the bite bumper strikes the occlusal surface of the upper tooth, preventing jaw closure. In order for the patient to comfortably close the teeth together, the lower jaw must be protruded forward, allowing the bumper to slip into the adjacent opening directly anterior to the upper tooth to be distalized. In this closed, corrected biting position, the lower jaw is held forward, and the upper tooth is urged distally by the bite bumper.

The device and method of this invention offer several advantages over traditional methods. This invention does not connect the jaws, allowing greater jaw movement, and allows the teeth in both arches to be moved orthodontically while the device is protracting the lower jaw. Having only one functional member for each side of the mouth, the device is simple in design, allowing it to be prefabricated rather than requiring manual laboratory construction. Additionally, the device prevents breakage of the tooth attachment by transmitting the vertical biting force near the clinical crown of the lower molar, rather than laterally near the cheek as with traditional devices. Because the device is positioned on the lower posterior teeth, it is invisible to the casual observer, enhancing patient appeal and esthetics. Being non-removable, compliance with the device and method is ensured. And finally, because this invention does not involve parts projecting toward the cheek, and is not bulky in the roof of the mouth, the patient experiences improved comfort and speech, and better oral hygiene.

DRAWINGS

FIG. 7 is a buccal view of another embodiment of a left-side device fixed to the lower left first permanent molar of a juvenile patient.

FIG. 7-A is a buccal, perspective view of a maxillary molar band having an occlusal wire.

FIG. 8 is a buccal view of another embodiment of a left-side device having a stainless steel veneer crown as a tooth attachment.

FIG. 9 is a perspective view of another embodiment of a left-side device having an adjustable and removable bumper unit.

FIG. 10 is a perspective view of another embodiment of a left-side device having a hinged bumper unit.

Figure 11:
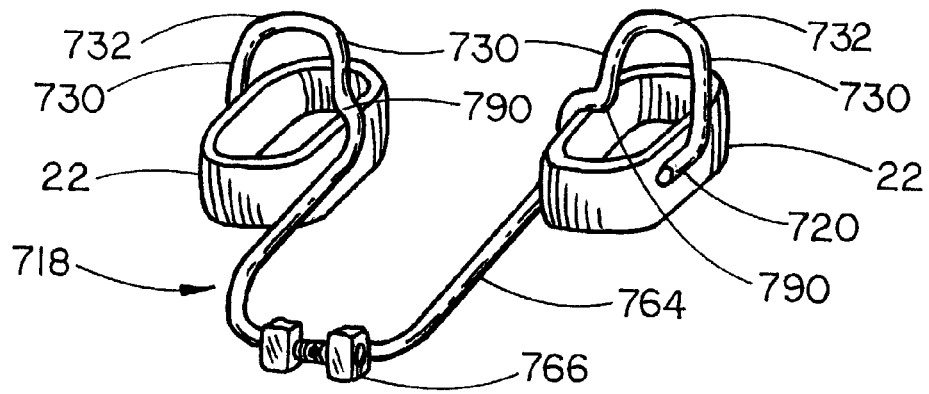

FIG. 11 is a perspective view of another embodiment including bilateral bite bumpers connected by a stiff lingual arch wire.

Figure 12:
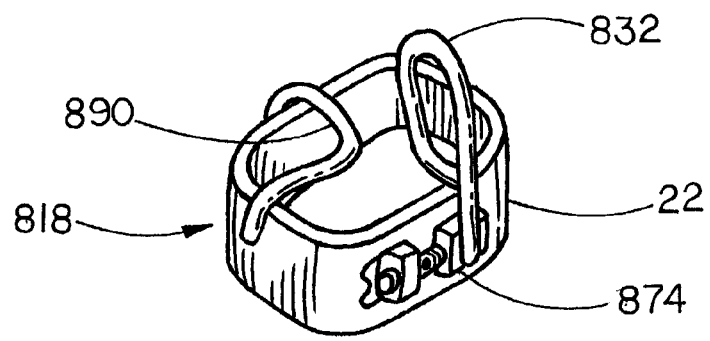

FIG. 12 is a perspective view of another embodiment of a left-side device having a sagittal turn screw as a mounting base.

Figure 13:
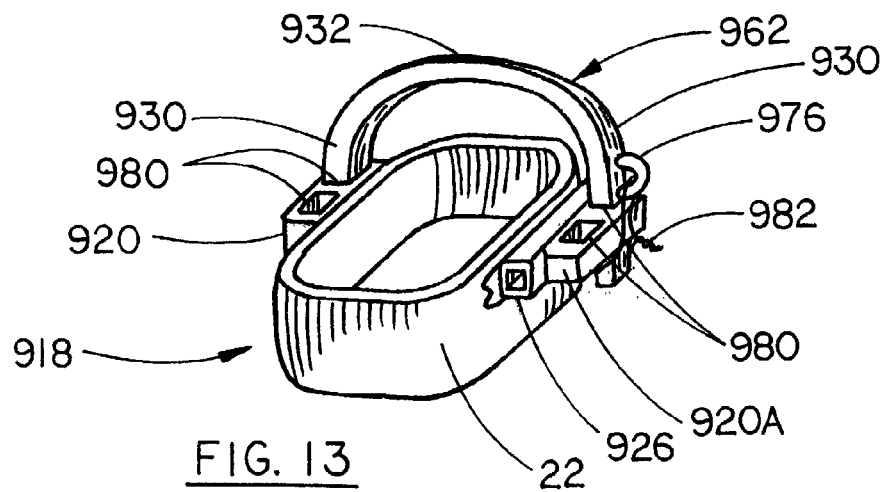

FIG. 13 is a perspective view of an additional embodiment of a left-side device having a removable bumper unit.

DESCRIPTION

Figure 1:
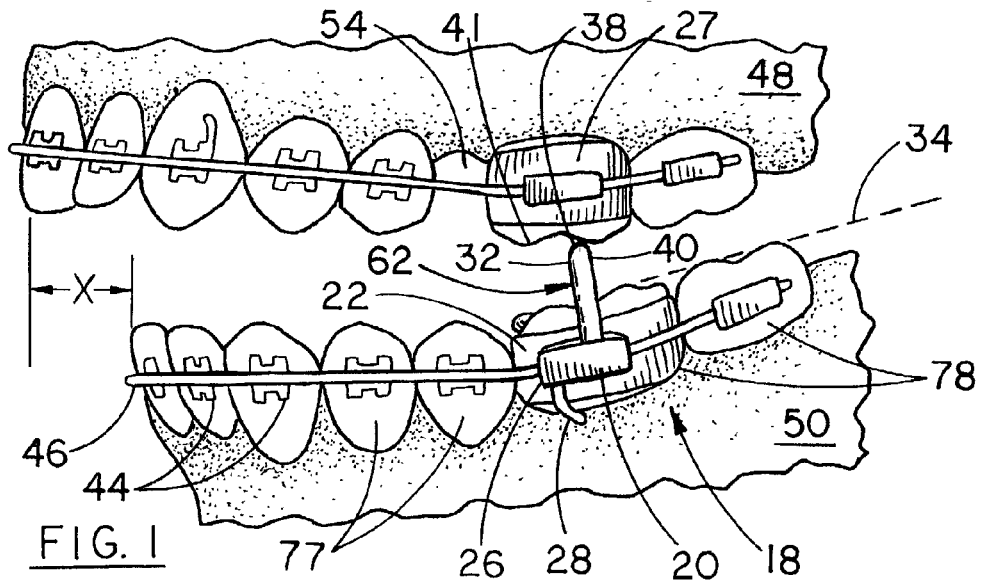
FIG. 1 is a buccal or cheek-side view of an embodiment of the present invention fixed to the lower left first molar of a patient having a malocclusion, with the retrusive lower jaw in its uncorrected position.

FIG. 1 shows a buccal or cheek-side view of the present device 18 mounted to the lower left first molar of a patient having a horizontal overbite, or "overjet", in which the mandibular jaw 50 is in a retruded, uncorrected position, as shown by the distance X. Device 18 includes a tooth attachment 22 for attaching device 18 to a lower posterior tooth. Attachment 22 is similar in metallic composition and size to most commercially available orthodontic bands. These bands are used for full-braces orthodontic treatment, and are generally composed of a stainless-steel alloy. Fixed to attachment 22 is a mounting base 20 comprising an edgewise molar tube 26. Mounting base 20 gives attachment to a bumper unit 62, which includes two holding legs 30–30 and a bite bumper 32. Holding legs 30–30 hold bite bumper 32 at a position above the mandibular occlusal plane 34. Bite bumper 32 has an obstruction surface 38, preferably having a vertical height measurement of about 5 mm above the occlusal (top) edge of attachment 22.

As depicted in FIG. 1, device 18 is positioned so as to place obstruction surface 38 of bumper 32 in contact with the maxillary occlusal surface 41 of the upper first molar when the mandibular jaw 50 is in the uncorrected position. When the patient attempts to close the maxillary jaw 48 and mandibular jaw 50 in the uncorrected position, obstruction surface 38 prevents complete closure of the jaws. This is generally an uncomfortable position for the patient, causing the patient to instinctively protrude the mandibular jaw 50 into a protrusive, corrected jaw position.

Figure 2:
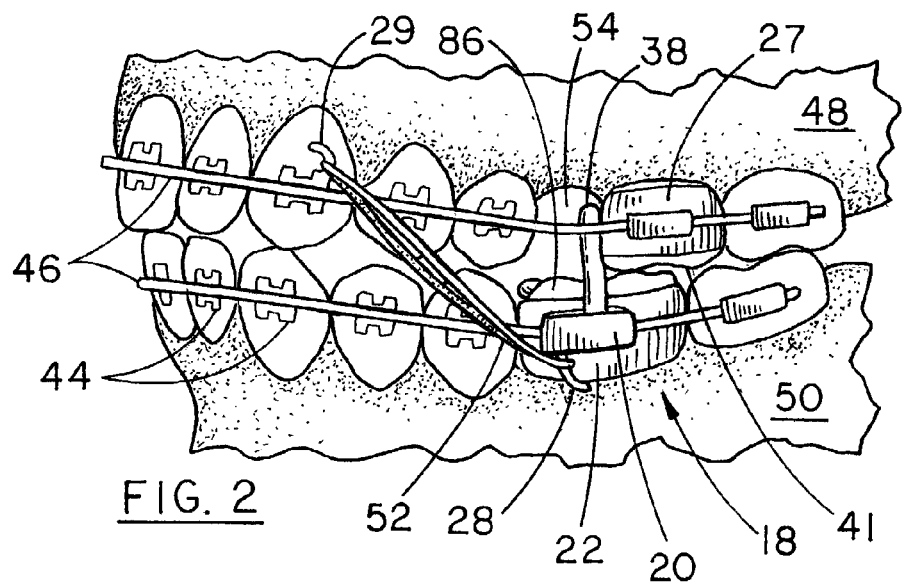
FIG. 2 is a buccal view of the same embodiment, shown with the lower jaw in a corrected position and the jaws in a closed relationship.

With the mandibular jaw 50 in the corrected position, as shown in FIG. 2, bite bumper 32 dears the upper first molar, sliding into the adjacent opening 54, just anterior to the upper first molar. This allows the abutment surface 40 of bite bumper 32 to contact the mesial or anterior surface of the upper first molar. In FIGS. 1 and 2, a maxillary molar band 27 encompasses the upper first molar tooth, covering its mesial surface. An orthodontic arch wire 46 and orthodontic brackets 44 can be used simultaneously with device 18 to align the other teeth while the bite is being corrected. Usually device 18 is attached to the lower first molar, but depending on the particular condition being treated, other teeth may be used instead. Generally device 18 is used with a corresponding device on the right side of the patient's mouth. However, depending on the particular needs of the patient, the device may be used only on a single side of a patient's mouth.

Referring to FIGS. 1 and 2, bumper unit 62 is preferably fabricated of a 0.040"-diameter, stainless-steel wire. Alternatively, unit 62 could be fabricated from a heat-treated, chrome-cobalt alloy wire, for ease of forming the wire, and could have a diameter between 0.030" and 0.040". Mounting base 20 is ideally an edgewise molar tube 26 for receiving orthodontic arch wire 46 which can be used for aligning the teeth along side the lower first molar. The tube opening of mounting base 20 could be fabricated in a standard, commercially available orthodontic size such as 0.018"×0.025"; or 0.022"×0.028". Although device 18 is mounted on the mandibular first molar, in other cases it could be mounted on either mandibular molar tooth 78–78, or either mandibular bicuspid tooth 77–77.

Figure 3:
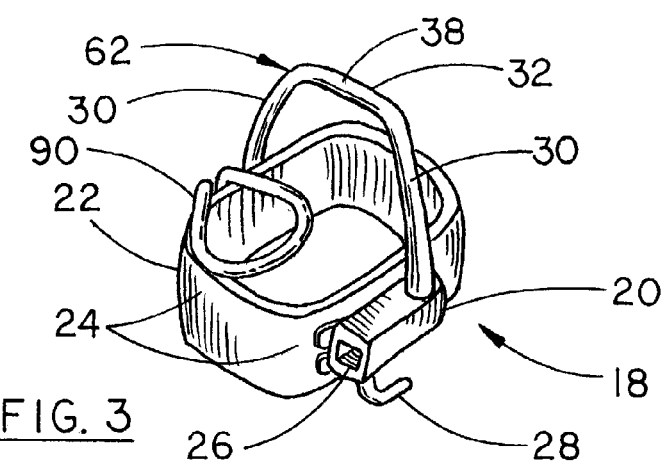
FIG. 3 is a perspective view of the same embodiment of a left-side version of the device for a lower left posterior tooth.

Referring now to FIG. 3, mounting element 20 is attached to the outer surface 24 of tooth attachment 20. Device 18 has a hook 28 for connecting an elastic band 52 which can be stretched forward and upward to the upper anterior tooth, thereby further correcting the bite by reducing the overjet. Band 52 is preferably a latex rubber band, commercially available for orthodontic use. Bite bumper 32 and holding legs 30—30 are fabricated from a continuous wire, forming a smooth semi-circular arch, which maximizes patient comfort. A halo-shaped occlusal rest 90 is fixed to the lingual surface of attachment 20, and encircles the mesial-lingual cusp of the lower first molar tooth when fully cemented in place. Rest 90 is preferably made of a stainless-steel wire having a diameter from 0.028" to 0.036". Occlusal rest 90 serves to prevent downward slippage of attachment 20 on the lingual surface of the molar, and enhances its retention strength on the molar during biting. Although device 18 includes two separate wires to create bumper unit 62 and rest 90, it is understood that an alternative embodiment could use one continuous wire to form unit 62 and rest 90. Furthermore, a metal-alloy casting or sintering technique could be used to fabricate unit 62 and rest 90 in one contiguous unit, which would then be fixed to attachment 20.

Figure 4:
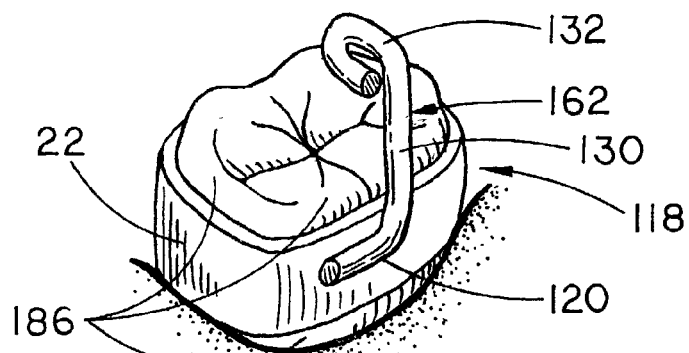
FIG. 4 is a buccal or cheek-side, perspective view of another embodiment of a left-side device for a lower left molar tooth.

Referring to FIG. 4, an alternative embodiment 118 of a left-side device of this invention is illustrated, in which bite bumper 132 is attached to tooth attachment 22 by only one holding leg 130. Mounting base 120 is an extension of the stainless-steel wire used to form bumper unit 162. When the patient bites down in the retruded or uncorrected jaw position, a strong downward biting force is transmitted to bite bumper 132. The lower posterior molar tooth has a clinical crown 186, which includes all five enamel surfaces visible in the mouth: the buccal, mesial, distal, lingual, and occlusal surfaces. Because bumper 132 is located vertically over the clinical crown 186, rather than laterally near the cheek, torsion force is minimized to attachment 22, decreasing breakage compared to traditional devices.

Figure 5:
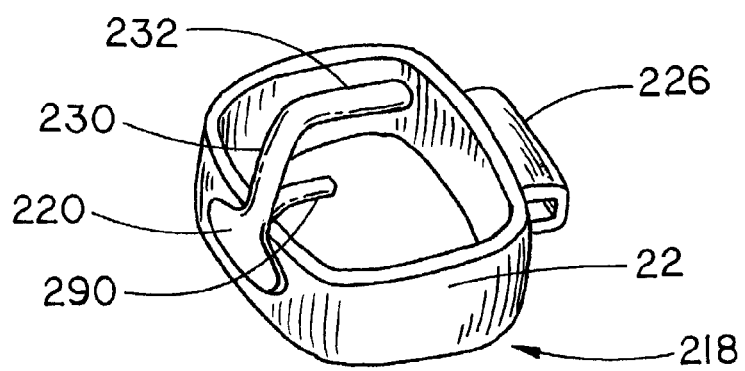
FIG. 5 is a lingual or tongue-side, perspective view of another embodiment of the device for a lower left molar tooth.

Referring to FIG. 5, an additional embodiment 218 of a left-side device is shown, with a mounting base 220 connected to the lingual or tongue-side surface of tooth attachment 22. Mounting base 220 has less thickness than holding leg 230 or bite bumper 232, providing improved patient hygiene and comfort. A molar tube 226 is mounted on the buccal surface of attachment 22 for holding an orthodontic arch wire. An occlusal rest 290, preferably formed of a 0.030 wire soldered to holding leg 230, increases stabilization and retention of attachment 22 on the lower posterior tooth.

Figure 6:
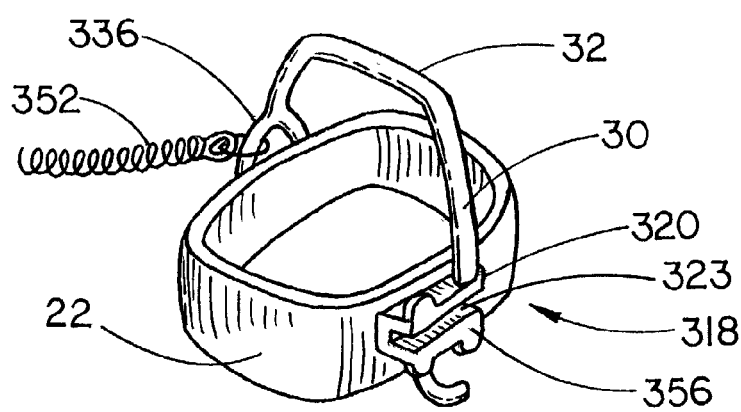
FIG. 6 is a perspective view of another embodiment of a left-side device having an elastic-element connector.

Referring to FIG. 6, another embodiment 318 of a left-side version of the device is illustrated. Mounting base 320 consists of an orthodontic molar bracket 356 with an open slot 323 for receiving an orthodontic arch wire. In this embodiment, elastic element 352 is depicted as a nickel-titanium closed coil. A connector 336 on the lingual surface of attachment 22 gives attachment to elastic element 352 which stretches to the upper anterior teeth for reducing the overjet.

Referring to FIG. 7, an alternative embodiment 398 of the device is shown fixed to a lower left permanent molar tooth of a juvenile patient also having four left primary molar teeth 42—42—42—42, which would eventually be lost and replaced by four new permanent teeth. Embodiment 398 is illustrated with maxillary tooth band 27, which includes an occlusal wire 29. Preferably fabricated of stainless-steel wire with a diameter less than 0.036", occlusal wire 29 serves to further inhibit jaw closure in the uncorrected jaw position. When bite bumper 32 contacts wire 29, the mandibular jaw 50 is guided forward to the corrected position. Unlike the embodiment shown in FIG. 1, bumper unit 363 of embodiment 398 is not centered from anterior to posterior, but is located close to the anterior surface of the lower first permanent molar. This bite relationship, with the upper and lower first permanent molars nearly end-on, is normal for a juvenile patient having both permanent and primary teeth. An inclined plane 339 is fabricated into bumper unit 363 to prevent unwanted bending of band 27 at its mesial occlusal edge when the patient bites together.

Referring to FIG. 7-A, maxillary tooth band 27 is illustrated from a buccal, perspective view. Referring also to FIG. 7, occlusal wire 29 enhances the function of bite bumper 32 by inhibiting jaw closure in the uncorrected jaw position, and by guiding bumper 32 anteriorly, resulting in protraction of mandibular jaw 50 to the corrected jaw position. Wire 29 also stabilizes and strengthens band 27, as well as increasing its retention on the upper first molar tooth.

Referring now to FIG. 8, another embodiment 418 of the device is illustrated. In this embodiment, a stainless steel veneer crown 472 having a veneer occlusal surface 473 serves to attach embodiment 418 to the lower molar tooth. The greater surface coverage of crown 472 has the advantages of less breakage and increased retention on the molar tooth. Bumper unit 462 is attached to veneer occlusal surface 473 of crown 472. Holding plate 430 is a metallic, triangular plate, extending vertically and giving attachment to a spherical bite bumper 432. Crown 472 is a commercially-available, stainless-steel veneer crown, commonly used to restore decayed primary teeth in children.

Referring to FIG. 9, another embodiment 518 of the device is illustrated, in which bumper unit 562 is formed of rectangular wire, and is removable. Mounting bases 520—520 have rectangular lumens, and are attached to the lingual and buccal surfaces of tooth attachment 522. Removal of unit 562 allows the clinician to verify the patient's bite relationship in a relaxed jaw position, without interference from bite bumper 532. The sagittal position of bumper unit 562 may be adjusted by sliding the ends of unit 562 forwardly or rearwardly through mounting bases 520—520. Adjusting unit 562 to a more posterior position causes a greater protrusion of the patient's mandibular jaw 50, thereby increasing the distalizing force to the upper posterior tooth. Ligature ties 582—582 are connected through unit holes 584—584 and tube holes 585—585, serving to prevent bumper unit 562 from becoming disconnected from mounting bases 520—520. Device 518 also includes occlusal rest 590 to increase stabilization and retention of tooth attachment 522 on the lower posterior tooth.

Referring to FIG. 10, an additional embodiment 618 of the device is shown in which mounting base 620 includes a hinge tube 660 having a round cross-sectional opening. Holding leg 630 attaches to tube 660 by a pair of hinge fingers 668—668. Bite bumper 632 can be hinged open by pulling the terminal end of bumper 632 out of a receiving cavity 670. By swinging bumper 632 upwardly and outwardly toward the cheek of the patient, the dental bite of the patient can be verified in a fully relaxed, uncorrected position of the jaws. After the dentist verifies the dental bite, holding leg 630 and bumper 632 are swung back into position by inserting the end of bumper 632 into receiving cavity 670.

Referring now in detail to FIG. 11, an alternative embodiment 718 of the device is shown, designed for attachment to the lower right and lower left first permanent molars. Holding legs 730—730—730—730 establish the vertical height for bite bumpers 732—732. This embodiment has a stiff lingual wire 764 which connects left and right tooth attachments 22—22. Lingual wire 764 rests alongside the tongue of the patient, contacting the lingual, or tongue-side, surface of the patient's lower teeth, and has an expansion screw 766 located near its center. Screw 766 can be turned with a key by the patient or dentist, causing transverse expansion of the lower arch to relieve dental crowding. This embodiment also has a pair of occlusal rests 790—790, formed by placing bends in the inner holding legs 730—730, which prevent downward slippage of attachments 22—22.

Referring now to FIG. 12, an alternative embodiment 818 of the device is shown, having a sagittal turn screw 874. The mesial or anterior portion of screw 874 is permanently mounted to attachment 22, allowing the posterior portion to slide sagittally (frontward or backward), when adjusted by turning. This allows for adjustment of the sagittal position of bite bumper 832, thereby causing greater or lesser degrees of mandibular protraction. In general, bumper 832 would be positioned more anteriorly, and then as treatment proceeds, screw 874 would be turned to move bumper 832 more posteriorly, thereby causing greater mandibular activation. This embodiment also has occlusal rest 890 for increasing stabilization and retention of attachment 22. Rest 890 is formed of a soldered wire having a diameter of between 0.028" and 0.032". When attached to the lower molar, rest 890 encircles the mesial-lingual cusp of the molar.

Referring now to FIG. 13, an additional embodiment 918 of a left-side device is shown, having a removable bumper unit 962. Removal of unit 962 allows the clinician to verify the patient's bite relationship in the relaxed, uncorrected jaw position. Lingual mounting base 920 and buccal mounting base 920A facilitate removal of unit 962 in a vertical direction. After verification of the patient's bite, the dentist replaces unit 962 by sliding holding legs 930—930 downward into bases 920 and 920A. Base 920A also includes an orthodontic tube 926 for holding an orthodontic arch wire. As a connector to prevent separation of unit 962 from bases 920 and 920A, a steel ligature tie 982 is tied through eyelet 976 and connected to base 920A or to the inferior end of unit 962. Mounting bases 920 and 920A each have two mounting lumens 980—980, allowing the sagittal position of bumper 932 to be adjustable by inserting holding legs 930—930 into either the anterior pair, or the posterior pair, of lumens 980—980. This ability of bumper 932 to be adjusted allows for two different amounts of mandibular protrusion, depending on the needs of the patient's dental bite.

OPERATION

In operation, device 18 as shown in FIG. 1, is attached to a lower posterior tooth, generally the lower first molar tooth, using a dental cement such as a composite glass ionomer cement, commercially available from most dental supply companies. Alternatively, device 18 can be cemented with a light-cured, bonded composite to increase retention strength. Prior to the cementation of this device, adjacent opening 54 is created just anterior to the upper posterior tooth to be distalized, usually between the upper first molar and the upper second bicuspid tooth. Opening 54 should be greater than 1 mm, preferably measuring 3 mm in anterior-posterior dimension. Opening 54 can be created with orthodontic braces having brackets 44 and arch wire 46, and using an opening mechanism such as a coil spring on arch wire 46. Another method for creating adjacent opening 54 is to use a fixed intraoral distalizing appliance such as a Hilgers pendulum or a Jones jig. Alternatively, in a patient having severe dental crowding, opening 54 may be created by extracting a tooth just anterior to the upper posterior tooth.

Once device 18 is cemented to the lower posterior tooth, bite bumper 32 will obstruct closure of the jaws when the mandibular jaw 50 is in the uncorrected, retrusive position. Because this position is generally uncomfortable and unstable, the patient protrudes the mandibular jaw 50, as shown in FIG. 2, causing bite bumper 32 to move anterior to the upper first molar. Bumper 32 then slides upwardly into opening 54, making contact with the mesial (anterior) surface of the upper first molar, or with its molar band 27. The jaw muscles and cheek tissues of the mandibular jaw 50 have elastic memory, and, when protruded in this manner, generate a responsive pressure to pull the mandibular jaw posteriorly towards its retrusive position. This posteriorly directed pressure is transmitted to the upper posterior teeth by way of device 18, specifically by bite bumper 32 pressing against the mesial surface of the upper molar. Over a period of time, generally between nine and fourteen months, the upper teeth move posteriorly and the lower teeth and jaw move anteriorly, shifting the bite into a corrected bite position. During this time, if needed, the bite correction can be enhanced by using a removable, latex elastic band 52, which attaches from hook 28 on the device to hook 29 on the upper anterior teeth.

After the molar bite correction has been accomplished, and the corrected jaw position remains stable, bite bumper 32 and holding legs 30—30 can be removed by dipping with a sturdy wire cutter. Alternatively, the entire device 18 can be removed, and replaced with a standard orthodontic band. At this point, treatment is finalized by closure of opening 54 using orthodontic arch wire 46 with elastic closing chain attached to brackets 44. After closure of opening 54, brackets 44 are removed from the patient's teeth, completing treatment.

While the invention has been disclosed in its preferred embodiments, it will be apparent to those skilled in the art that many modifications, additions, and deletions can be made therein without departing from the spirit and scope of the invention and its equivalents set forth in the following claims.

What is claimed is:

1. A device for assisting a patient in maintaining a protraction force on the patient's mandibular jaw, and in maintaining a posteriorly-directed force on a maxillary posterior first tooth in the patient's maxillary jaw, said first tooth having a mesial surface and a maxillary occlusal surface, said maxillary jaw having an adjacent opening between said posterior first tooth and an adjacent forward second tooth, said mandibular jaw including a mandibular occlusal plane and a mandibular posterior third tooth having a clinical crown, said jaws having corrected and uncorrected positions, said device comprising:

a lower tooth attachment having an outer surface, for connecting said device to said third tooth;
   a mounting means connected to said outer surface of said lower tooth attachment;
   a bumper unit, further comprising:
      at least one holding means connected to said mounting means; and
      a bite bumper fixed to said holding means including an abutment surface and an obstruction surface, and means for disposing said obstruction surface at a predetermined vertical height over a mandibular occlusal plane, and being receivable in an opening between said posterior first tooth and an adjacent forward tooth as a patient's jaw is moved to a fully closed position in which teeth in mandibular jaw contact teeth on the maxillary jaw;
   said device attachable to said third tooth, so as to place said obstruction surface in contact with said maxillary occlusal surface of said first tooth when said mandibular jaw is in said uncorrected position, causing said obstruction surface to strike said maxillary occlusal surface when the patient attempts to close said jaws in said uncorrected position, thereby preventing complete closure of said jaws unless said mandibular jaw is protracted in an anterior direction from said uncorrected position sufficient to allow said bite bumper to clear said maxillary occlusal surface, at which point the patient may close said jaws in said corrected position, bringing said bite bumper into said adjacent opening, and bringing said abutment surface of said bite bumper into contact with said mesial surface of said first tooth;
   said tooth attachment being an annular orthodontic band having an opening for the occlusal surface of said clinical crown; and
   including an occlusal rest connected to said orthodontic band, for increasing the retention and stability of said tooth attachment on said third tooth; and
   whereby said first tooth is urged posteriorly, said mandibular jaw is urged anteriorly, and over a period of time said jaws and teeth become stable in said corrected position.

2. The device of claim 1, wherein said tooth attachment is a metallic veneer crown, having a veneer occlusal surface, for increasing the strength and retention of said tooth attachment on said third tooth.

3. The device of claim 2, wherein said mounting means is attached to said veneer occlusal surface of said metallic veneer crown.

4. The device of claim 1, wherein said bumper unit is capable of adjustment in an anterior-posterior direction, for allowing variable amounts of mandibular protraction when the patient closes said jaws in said corrected position, depending on the individual needs of the patient.

5. The device of claim 1, wherein said mounting means comprises an orthodontic bracket capable of receiving an orthodontic arch wire, for improving the alignment of said mandibular third tooth and the other mandibular teeth in said mandibular jaw.

6. The device of claim 1, further including a second mounting means fixed to the lingual portion of said outer surface of said tooth attachment, and a second holding means connected to said second mounting means, said second holding means being attachable to said bite bumper, for further strengthening said bumper unit.

7. The device of claim 1, wherein said bumper unit is removable from said mounting means, for allowing the dentist to verify the patient's dental bite with said jaws in said uncorrected position.

8. The device of claim 1, including a maxillary molar band having an occlusal edge, and means for attaching said maxillary molar band to said first tooth, and said bite bumper further comprises an inclined plane for preventing unwanted damage or bending of said occlusal edge of said maxillary molar band when the patient bites together with said bite bumper in contact with said occlusal edge.

9. A method of assisting a patient in maintaining a protraction force on the patient's mandibular jaw, and in maintaining a posteriorly-directed force on a posterior first tooth in the patient's maxillary jaw, said first tooth having a mesial surface and a maxillary occlusal surface, said maxillary jaw having an adjacent opening between said first tooth and an adjacent forward second tooth, said mandibular jaw including a mandibular occlusal plane and a mandibular posterior third tooth having a clinical crown, said jaws having corrected and uncorrected positions, comprising the steps of:

mounting a bite bumper having an abutment surface on a third tooth in the patient's mandibular jaw, said bumper extending vertically from said third tooth to said first tooth; and closing the mandibular jaw toward the maxillary jaw until said bite bumper engages said maxillary occlusal surface of said first tooth, and continuing to close the mandibular jaw such that said bumper slides forwardly on said first tooth and moves to a position in said opening between said first tooth and said second tooth, bringing said abutment surface into contact with said mesial surface of said first tooth; and whereby said first tooth is urged posteriorly, said mandibular jaw is urged anteriorly, and over a period of time said jaws and teeth become stable in said corrected position.

10. The method of claim 9, further including the step of providing said adjacent opening before the step of mounting said bite bumper, said adjacent opening provided by moving said first tooth posteriorly with a fixed intraoral distalizing device.

11. The method of claim 9, further including the step of providing said adjacent opening before the step of mounting said bite bumper, said adjacent opening provided by moving said first tooth posteriorly and said second tooth anteriorly using an orthodontic arch wire and orthodontic brackets attached to the patient's maxillary teeth.

12. The method of claim 9, wherein said maxillary first tooth includes a maxillary tooth attachment further comprising an occlusal wire for guiding said bite bumper into said adjacent opening during closure of said jaws in said corrected position.

13. The method of claim 9, wherein said method is performed to treat a condition selected from the group of overbite, overjet, mandibular retrusion, class II molar relationship, forward relapse of said first tooth following distalization, and combinations thereof.

14. A device for assisting a patient in maintaining a protraction force on the patient's mandibular jaw, and in maintaining a posteriorly-directed force on a maxillary posterior first tooth in the patient's maxillary jaw, said first tooth having a mesial surface and a maxillary occlusal surface, said maxillary jaw having an adjacent opening between said posterior first tooth and an adjacent forward second tooth, said mandibular jaw including a mandibular occlusal plane and a mandibular posterior third tooth having a clinical crown, said jaws having corrected and uncorrected positions, said device comprising:

a single tooth attachment comprising an annular orthodontic band having an opening for the occlusal surface of said clinical crown, and having an outer surface, for connecting said device to said third tooth, and an occlusal rest connected to said orthodontic band, for increasing the retention and stability of said tooth attachment on said third tooth;

a mounting means connected to said outer surface of said tooth attachment;

a bumper unit, further comprising:

at least one holding means connected to said mounting means; and a bite bumper fixed to said holding means including an abutment surface and an obstruction force and means for disposing said obstruction surface at a predetermined vertical height over a mandibular occlusal plane;

said device attachable to said third tooth, so as to place said obstruction surface in contact with said maxillary occlusal surface of said first tooth when said mandibular jaw is in said uncorrected position, causing said obstruction surface to strike said maxillary occlusal surface when the patient attempts to close said jaws in said uncorrected position, thereby preventing complete closure of said jaws unless said mandibular jaw is protracted in an anterior direction from said uncorrected position sufficient to allow said bite bumper to clear said maxillary occlusal surface, at which point the patient may close said jaws in said corrected position, bringing said bite bumper into said adjacent opening, and bringing said abutment surface of said bite bumper into contact with said mesial surface of said first tooth; and whereby said first tooth is urged posteriorly, said mandibular jaw is urged anteriorly, and over a period of time said jaws and teeth become stable in said corrected position.

15. A device for assisting a patient in maintaining a protraction force on the patient's mandibular jaw, and in maintaining a posteriorly-directed force on a maxillary posterior first tooth in the patient's maxillary jaw, said first tooth having a mesial surface and a maxillary occlusal surface, said maxillary jaw having an adjacent opening between said posterior first tooth and an adjacent forward second tooth, said mandibular jaw including a mandibular occlusal plane and a mandibular posterior third tooth having a clinical crown, said jaws having corrected and uncorrected positions, said device comprising:

a single tooth attachment having an outer surface, for connecting said device to said third tooth;

a mounting means connected to said outer surface of said tooth attachment;

a bumper unit, further comprising:

at least one holding means connected to said mounting means; and a bite bumper fixed to said holding means including an abutment surface and an obstruction surface, and means for disposing said obstruction surface at a predetermined vertical height over a mandibular occlusal plane, and being receivable in an opening between said posterior first tooth and an adjacent forward tooth as a patient's jaw is moved to a fully closed position in which teeth in mandibular jaw contact teeth on the maxillary jaw;

said device being attachable to said third tooth, to place said obstruction surface in contact with said maxillary occlusal surface of said first tooth when said mandibular jaw is in said uncorrected position, causing said obstruction surface to strike said maxillary occlusal surface when the patient attempts to close said jaws in said uncorrected position, thereby preventing complete closure of said jaws unless said mandibular jaw is protracted in an anterior direction from said uncorrected position sufficient to allow said bite bumper to clear said maxillary occlusal surface, at which point the patient may close said jaws in said corrected position, bringing said bite bumper into said adjacent opening, and bringing said abutment surface of said bite bumper into contact with said mesial surface of said first tooth;

whereby said first tooth is urged posteriorly, said mandibular jaw is urged anteriorly, and over a period of time said jaws and teeth become stable in said corrected position; and said holding means is hinged, for allowing said bumper unit to be swung away from the occlusal surface of said third tooth, thereby enabling the dentist to verify the patient's dental bite with said jaws in said uncorrected position.

16. A device for assisting a patient in maintaining a protraction force on the patient's mandibular jaw, and in maintaining a posteriorly-directed force on a maxillary posterior first tooth in the patient's maxillary jaw, said first tooth having a mesial surface and a maxillary occlusal surface, said maxillary jaw having an adjacent opening between said posterior first tooth and an adjacent forward second tooth, said mandibular jaw including a mandibular occlusal plane and a mandibular posterior third tooth having a clinical crown, said jaws having corrected and uncorrected positions, said device comprising:
- a lower tooth attachment having an outer surface, for connecting said device to said third tooth;
- a mounting means connected to said outer surface of said lower tooth attachment;
- a bumper unit, further comprising:
  - at least one holding means connected to said mounting means; and
  - a bite bumper fixed to said holding means including an abutment surface and an obstruction surface, and means for disposing said obstruction surface at a predetermined vertical height over a mandibular occlusal plane, and being receivable in an opening between said posterior first tooth and an adjacent forward tooth as a patient's jaw is moved to a fully closed position in which teeth in mandibular jaw contact teeth on the maxillary jaw;

said device attachable to said third tooth, so as to place said obstruction surface in contact with said maxillary occlusal surface of said first tooth when said mandibular jaw is in said uncorrected position, causing said obstruction surface to strike said maxillary occlusal surface when the patient attempts to close said jaws in said uncorrected position, thereby preventing complete closure of said jaws unless said mandibular jaw is protracted in an anterior direction from said uncorrected position sufficient to allow said bite bumper to clear said maxillary occlusal surface, at which point the patient may close said jaws in said corrected position, bringing said bite bumper into said adjacent opening, and bringing said abutment surface of said bite bumper into contact with said mesial surface of said first tooth;

said holding means being hinged, for allowing said bumper unit to be swung away from the occlusal surface of said third tooth, thereby enabling the dentist to verify the patient's dental bite with said jaws in said uncorrected position; and whereby said first tooth is urged posteriorly, said mandibular jaw is urged anteriorly, and over a period of time said jaws and teeth become stable in said corrected position.

* * * * *